United States Patent
Lee

(10) Patent No.: US 8,529,832 B2
(45) Date of Patent: Sep. 10, 2013

(54) METHODS OF STERILIZATION BY HYDROGEN PEROXIDE AND OZONE, AND APPARATUS USING THE METHODS

(75) Inventor: Kwang-Sik Lee, Incheon (KR)

(73) Assignee: Renosem Co., Ltd., Incheon (KR)

( * ) Notice: Subject to any disclaimer, the term of this patent is extended or adjusted under 35 U.S.C. 154(b) by 323 days.

(21) Appl. No.: 12/665,939

(22) PCT Filed: Jun. 27, 2008

(86) PCT No.: PCT/KR2008/003716
§ 371 (c)(1),
(2), (4) Date: Dec. 22, 2009

(87) PCT Pub. No.: WO2009/005252
PCT Pub. Date: Jan. 8, 2009

(65) Prior Publication Data
US 2011/0008209 A1    Jan. 13, 2011

(30) Foreign Application Priority Data
Jun. 29, 2007    (KR) ........................ 10-2007-0065359

(51) Int. Cl.
*A61L 9/00*    (2006.01)
*A61L 2/00*    (2006.01)
*A61L 2/18*    (2006.01)
*A61L 2/20*    (2006.01)

(52) U.S. Cl.
USPC .................... 422/29; 422/28; 422/30; 422/33

(58) Field of Classification Search
USPC ............... 422/28, 30, 33, 292, 295, 298, 299, 422/29
See application file for complete search history.

(56) References Cited

U.S. PATENT DOCUMENTS

| | | | |
|---|---|---|---|
| 4,643,876 A | 2/1987 | Jacobs et al. | |
| 5,868,999 A * | 2/1999 | Karlson | 422/30 |
| 6,096,266 A * | 8/2000 | Duroselle | 422/33 |
| 6,365,103 B1 * | 4/2002 | Fournier | 422/33 |
| 2008/0233002 A1 * | 9/2008 | Mizuno et al. | 422/22 |
| 2009/0263499 A1 * | 10/2009 | Platt et al. | 424/616 |

FOREIGN PATENT DOCUMENTS

| | | | |
|---|---|---|---|
| JP | 10117752 A | * | 5/1998 |
| JP | 10038598 | | 8/1999 |
| JP | 11163486 | | 10/2000 |
| JP | 2000095666 | | 11/2000 |
| JP | 2001172532 | | 12/2002 |

(Continued)

OTHER PUBLICATIONS

English translation of JP 10-117752, May 1998.*

(Continued)

*Primary Examiner* — Regina M Yoo
(74) *Attorney, Agent, or Firm* — Mark M. Friedman

(57) ABSTRACT

A method for sterilization according to the present invention comprises: a first sterilization step of providing a sterilization subject in a sealed sterilization chamber and sterilizing the sterilization subject by providing ozone inside the sterilization chamber; a first decomposition step of decomposing the ozone inside the sterilization chamber; a first vacuumization step discharging the gas inside the sterilization chamber and reducing the pressure inside the sterilization chamber; a second sterilization step of providing hydrogen peroxide into the vacuumized sterilization chamber to sterilize the sterilization subject; a third sterilization step of providing ozone into the sterilization chamber; a second decomposition step of decomposing the hydrogen peroxide and ozone inside the sterilization chamber; and a second vacuumization step of discharging the gas inside the sterilization chamber and reducing the pressure inside the sterilization chamber.

6 Claims, 4 Drawing Sheets

(56) References Cited

FOREIGN PATENT DOCUMENTS

| KR | 1020067019980 | | 2/2007 |
|---|---|---|---|
| WO | WO 2005094907 A1 | * | 10/2005 |

OTHER PUBLICATIONS

English translation of KR 1020067019980, Feb. 2007.*
English translation of JP 11-226579, Aug. 1999.*

* cited by examiner

METHODS OF STERILIZATION BY HYDROGEN PEROXIDE AND OZONE, AND APPARATUS USING THE METHODS

TECHNICAL FIELD

The present invention relates to a method and an apparatus for sterilizing medical instruments and the like, particularly to a method and an apparatus for sterilization using hydrogen peroxide and ozone in order to maximize sterilization efficiency, reduce sterilization time and attain cost reduction.

BACKGROUND ART

With respect to sterilization of medical instruments, sterilization means a higher level treatment, differently from cleaning or disinfection, which refers to the complete elimination of all living microorganisms through physical or chemical action. At present, sterilization of medical instruments is carried out using ethylene oxide (EO) gas, steam, hydrogen peroxide, plasma, and so forth.

Recently, a new type of EO sterilizer which uses 100% EO gas and does no use CFC (chlorofluorocarbon) as carrier gas has emerged. However, as well known in the related art, EO gas is highly explosive. It is also reported that EO acts as genetically toxic substance resulting in mutations. In this regard, the American Conference of Governmental Industrial Hygienist (ACGIH) regulates the level of EO gas in working environments to be not greater than 1 ppm, and considers EO gas as potential carcinogen. However, with the new-type EO sterilizer, it is not easy to thoroughly control the level of EO gas below the allowed standard. Further, although the sterilization time was reduced, the sterilization time of the new-type EO sterilizer is still long at 3 to 5 hours.

Meanwhile, steam sterilization is evaluated as one of those methods that can satisfy a sterilization efficiency of a predetermined level and is safe. Steam sterilization is advantageous in that it is without toxicity, requires relatively low cost, and enables fast sterilization. However, a steam sterilizer can be used only for the medical instruments which are without problem when exposed to high humidity and temperature.

Also, a combination of hydrogen peroxide, ozone and plasma for sterilization is known in the related art. For example, a method of providing hydrogen peroxide in a sterilization chamber and generating plasma inside the sterilization chamber; a method of providing plasma and a steriliant simultaneously in a sterilization chamber; a method of providing oxygen in a sterilization chamber and transferring it to ozone by generating plasma; and a method of providing hydrogen peroxide along with ozone in a sterilization chamber; and so forth are known.

Further, a method of providing vaporized hydrogen peroxide in a sterilization chamber, followed by providing ozone to sterilize a sterilization subject, discharging gas out of the chamber, and decomposing hydrogen peroxide and ozone remaining near the sterilization subject by the plasma generated in the chamber is known in the art.

However, because the conventional sterilization apparatuses utilizing hydrogen peroxide, ozone and plasma are associated with a sterilization occurring at low, i.e., atmospheric, pressure, they provide relatively lower sterilization efficiency than the high-pressure apparatuses. Further, once sterilization begins, the air particles existing before the beginning of the sterilization interfere with the action of the steriliant, thereby decreasing sterilization efficiency. Besides, the fact that an expensive plasma apparatus is required to generate plasma in the sterilization chamber remains an obstacle in the wide spread of sterilization apparatuses in the medical field.

DISCLOSURE

Technical Problem

The present invention has been made in view of the problems of the conventional methods and apparatuses for sterilization. An object of the present invention is to provide a method for sterilization which can maximize sterilization efficiency while reducing sterilization time and significantly reducing manufacturing cost of a sterilization apparatus, and an apparatus utilizing the method.

Technical Solution

A method for sterilization according to an embodiment of the present invention to in order to attain the object comprises: a first sterilization step of providing a sterilization subject in a sealed sterilization chamber and sterilizing the sterilization subject by providing ozone inside the sterilization chamber; a first decomposition step of decomposing the ozone inside the sterilization chamber; a first vacuumization step discharging the gas inside the sterilization chamber and reducing the pressure inside the sterilization chamber; a second sterilization step of providing hydrogen peroxide into the vacuumized sterilization chamber to sterilize the sterilization subject; a third sterilization step of providing ozone into the sterilization chamber; a second decomposition step of decomposing the hydrogen peroxide and ozone inside the sterilization chamber; and a second vacuumization step of discharging the gas inside the sterilization chamber and reducing the pressure inside the sterilization chamber.

A method for sterilization according to the present invention in order to attain the object comprises: a first sterilization step of providing a sterilization subject in a sealed sterilization chamber and sterilizing the sterilization subject by providing ozone inside the sterilization chamber; a first decomposition step of decomposing the ozone inside the sterilization chamber; a first vacuumization step discharging the gas inside the sterilization chamber and reducing the pressure inside the sterilization chamber; a second sterilization step of providing hydrogen peroxide into the vacuumized sterilization chamber to sterilize the sterilization subject; a third sterilization step of providing ozone into the sterilization chamber; a second decomposition step of decomposing the hydrogen peroxide and ozone inside the sterilization chamber; and a second vacuumization step of discharging the gas inside the sterilization chamber and reducing the pressure inside the sterilization chamber.

In the method for sterilization according to the present invention, the steps from the first sterilization step through the second vacuumization step can be repeated until the wanted degree of sterilization is attained.

Preferably, the method for sterilization according to the present invention further comprises a pressure restoration step of restoring the pressure inside the sterilization chamber to atmospheric pressure after the second vacuumization step.

In the method for sterilization according to the present invention, the ozone provided in the first sterilization step may be produced by converting an oxygen-containing substance outside the sterilization chamber. In that case, it is preferred that the first sterilization step is carried out under the condition where the pressure inside the sterilization chamber is atmospheric pressure or higher.

Alternatively, the ozone provided in the first sterilization step may be produced by converting oxygen contained inside the sterilization chamber.

In the method for sterilization according to the present invention, the third sterilization step is preferably carried out under the condition where the pressure inside the sterilization chamber is atmospheric pressure or higher.

A mixed sterilization apparatus utilizing the method for sterilization according to the present invention comprises: a sterilization chamber which holds a sterilization subject and is sealed from outside; an ozone compressor which converts an oxygen-containing substance outside the sterilization chamber into ozone and provides it into the sterilization chamber; a vacuumization accelerator which vacuumizes the inside of the sterilization chamber; and a hydrogen peroxide vaporizer which vaporizes hydrogen peroxide and provides it into the sterilization chamber, wherein the vacuumization accelerator comprises an ozone decomposer which decomposes the ozone inside the sterilization chamber; and a hydrogen peroxide decomposer which decomposes the hydrogen peroxide inside the sterilization chamber.

A mixed sterilization apparatus utilizing the method for sterilization according to another embodiment of the present invention comprises: a sterilization chamber which holds a sterilization subject and is sealed from outside; an ozone compressor which converts oxygen inside the sterilization chamber into ozone and provides it into the sterilization chamber again; a vacuumization accelerator which vacuumizes the inside of the sterilization chamber; and a hydrogen peroxide vaporizer which vaporizes hydrogen peroxide and provides it into the sterilization chamber, wherein the vacuumization accelerator comprises an ozone decomposer which decomposes the ozone inside the sterilization chamber; and a hydrogen peroxide decomposer which decomposes the hydrogen peroxide inside the sterilization chamber.

Preferably, the mixed sterilization apparatus of the present invention further comprises a pressure restorer which restores the pressure inside the sterilization chamber to atmospheric pressure after a sterilization process is completed.

Further, preferably, the sterilization inside the sterilization chamber is carried out under the condition where the pressure inside the sterilization chamber is atmospheric pressure or higher.

Advantageous Effects

In accordance with the present invention, because of the first sterilization step of providing ozone inside a sterilization chamber and sterilizing a sterilization subject, more effective sterilization is possible through the major, second and third sterilization steps, and sterilization time can be reduced. Further, because no expensive equipment such as plasma generator is required to decompose hydrogen peroxide and ozone inside the sterilization chamber, cost for manufacture of the sterilization apparatus can be decreased significantly.

Because the sterilization steps according to the present invention are carried out under atmospheric pressure or above, or under at least substantially the same pressure as atmospheric pressure, much more effective sterilization is possible as compared to the conventional sterilization apparatus and method whereby sterilization occurs under a pressure below atmospheric pressure.

In addition, the cost can be further reduced, because an oxygen-containing substance outside the sterilization chamber may not be used to provide ozone. By converting oxygen inside the sterilization chamber into ozone, the interruption of sterilization by the steriliant by a gas other than the steriliant inside the sterilization chamber can be minimized.

DESCRIPTION OF DRAWINGS

The above and other objects, features and other advantages of the present invention will be more clearly understood from the following detailed description taken in conjunction with the accompanying drawings, in which.

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations and shapes will be determined in part by the particular intended application and use environment.

BEST MODE

Hereinafter, reference will be made in detail to preferred embodiments of the present invention, examples of which are illustrated in the accompanying drawings and described below.

Figure 1:
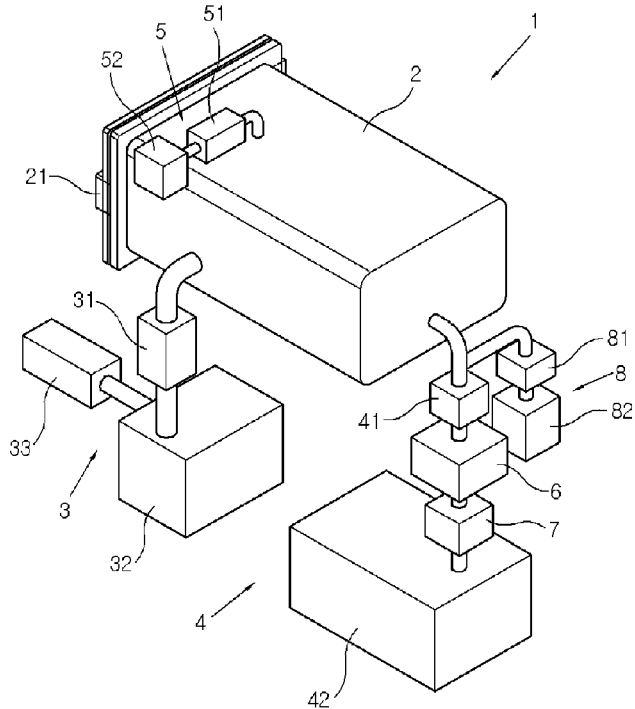
FIG. 1 schematically illustrates a mixed sterilization apparatus according to an embodiment of the present invention.

FIG. 1 schematically illustrates a mixed sterilization apparatus 1 using hydrogen peroxide and ozone according to an embodiment of the present invention. The mixed sterilization apparatus 1 comprises: a sterilization chamber 2 which holds a sterilization subject; an ozone compressor 3 which provides ozone into the sterilization chamber 2; a vacuumization accelerator 4 which sucks in the gas present inside the sterilization chamber 2 and vacuumizes the inside of the sterilization chamber 2; a hydrogen peroxide compressor 5 which vaporizes hydrogen peroxide and provides it into the sterilization chamber 2; and a pressure restorer 8 which restores the pressure inside the sterilization chamber 2 to atmospheric pressure after a sterilization process is completed.

The sterilization subject requiring sterilization, such as a medical instrument, is held inside the sterilization chamber 2 through a chamber door 21. After the chamber door 21 is closed, the sterilization chamber 2 is sealed from outside such that gas may not enter.

The ozone compressor 3 is connected at one side of the sterilization chamber 2. The ozone compressor 3 converts oxygen supplied from outside of the sterilization chamber 2 into ozone and provides it into the sterilization chamber 2. The oxygen supplied from outside of sterilization chamber 2 may be supplied using a common oxygen-containing substance. Examples of the oxygen-containing substance include water, air, hydrogen peroxide, and the like. In this embodiment, air outside the sterilization chamber 2 is used as oxygen-containing substance.

The ozone compressor 3 of this embodiment comprises an ozone generator 31, air supply pump 32 and a filter 33. The air supply pump 32 sucks in air outside the sterilization chamber 2 through a filter 33, and the ozone generator 31 converts oxygen contained in the air to ozone and provides it into the sterilization chamber 2. For example, the ozone generator 31 may be a plasma device.

The sterilization chamber 2 is also connected to the vacuumization accelerator 4. The vacuumization accelerator 4 sucks in the gas, e.g., air, remaining inside the sterilization chamber 2 before the sterilization process begins or the hydrogen peroxide, ozone and other gas flown into the sterilization chamber 2 during the sterilization process, and discharges it out of the sterilization chamber 2. The creation of vacuum inside the sterilization chamber 2 by discharging the gas remaining in the sterilization chamber 2 is to maximize sterilization efficiency by the ozone and/or hydrogen peroxide to be newly provided. The vacuumization accelerator 4 is equipped with a vacuum valve 41 and a vacuum pump 42. A hydrogen peroxide decomposer 6 and an ozone decomposer 7 are provided between the vacuum valve 41 and the vacuum pump 42 of the vacuumization accelerator 4. The hydrogen peroxide decomposer 6 and the ozone decomposer 7 decompose hydrogen peroxide and ozone into unharmful gas while the hydrogen peroxide and ozone used during the sterilization process are discharged out of the sterilization chamber 2. The decomposition of hydrogen peroxide may be carried out using, for example, a plasma generator (not illustrated in the figure), and the ozone may be decomposed using a heater, catalyst device (not illustrated in the figure), or the like.

The sterilization chamber 2 is connected to the hydrogen peroxide compressor 5 which vaporizes hydrogen peroxide and provides it into the sterilization chamber 2. The hydrogen peroxide compressor 5 comprises a hydrogen peroxide vaporizer 51 and a hydrogen peroxide supplier 52.

At last, the sterilization chamber 2 is equipped with a pressure restorer 8 which restores the pressure inside the sterilization chamber 2 to atmospheric pressure. In order to take out the sterilization subject, e.g., medical instrument, held inside the sterilization chamber 2 by opening the chamber door 21 of the sterilization chamber 2 after the sterilization process is completed, the pressure inside the sterilization chamber 2 has to be at least substantially the same as atmospheric pressure. This is attained by the pressure restorer 8. The pressure restorer 8 comprises a pressure restoration valve 81 and a filter 82, and is connected to the sterilization chamber 2.

Now, a sterilization process using the mixed sterilization apparatus of the present invention illustrated in FIG. 1 will be described referring to FIG. 2.

Firstly, a sterilization subject to be sterilized, e.g., medical instrument, is held inside the sterilization chamber 2 through the chamber door 21. Then, the chamber door 21 is closed to seal off the sterilization chamber 2. Subsequently, the ozone compressor 3 is operated to provide ozone onto the sterilization chamber 2. Then, a first sterilization step begins by the ozone provided into the sterilization chamber 2.

As described earlier, the ozone compressor 3 converts oxygen contained in an oxygen-containing substance outside the sterilization chamber 2 to ozone and provides it into the sterilization chamber 2. In this embodiment, oxygen included in air outside the sterilization chamber 2 is converted to ozone and is provided it into the sterilization chamber 2. Because the ozone converted from the oxygen-containing substance is provided into the sterilization chamber 2 after the sterilization chamber 2 is sealed off, the pressure inside the sterilization chamber 2 in the first sterilization step is higher than atmospheric pressure. In the first sterilization step of this embodiment, ozone is provided such that the pressure inside the sterilization chamber 2 is about 2 times the atmospheric pressure, i.e., 1500 torr. By providing the steriliant (ozone) such that the pressure inside the sterilization chamber 2 is above atmospheric pressure, sterilization efficiency of the sterilization subject can be increased as desired.

After carrying out the first sterilization step for a predetermined period of time, the ozone provided in first sterilization step is discharged out of the sterilization chamber 2. Prior to the discharge of ozone, the ozone discharged from the sterilization chamber 2 into the atmosphere passes through a ozone decomposer 7 in order to convert the ozone to unharmful substance (first decomposition step). The unharmful gas decomposed by the ozone decomposer 7 is completely discharged out of the sterilization chamber 2 by the operation of the vacuumization accelerator 4, and the pressure inside the sterilization chamber 2 is decreased to a substantial vacuum (first vacuumization step). In FIG. 2, the step during which the ozone inside the sterilization chamber 2 is decomposed and the pressure inside the sterilization chamber 2 is decreased is represented as "$O_3$ decomposition" step. The discharge of the gas remaining inside the sterilization chamber 2 and the lowering of the pressure inside the sterilization chamber 2 are to maximize sterilization efficiency of the steriliant, i.e., ozone and/or hydrogen peroxide, to be provided subsequently.

Next, the hydrogen peroxide compressor 5 is operated to vaporize hydrogen peroxide and provide it into the sterilization chamber 2 for a predetermined period of time. Through this, a second sterilization step is accomplished. Like the conventional sterilization apparatuses, the second sterilization step is carried out under the condition where the pressure inside the sterilization chamber 2 is atmospheric pressure.

After carrying out the second sterilization step for a predetermined period of time, the ozone compressor 3 is operated to provide ozone into the sterilization chamber 2 in which hydrogen peroxide is provided already. Through this, a third sterilization step by the action of hydrogen peroxide and ozone inside the sterilization chamber 2 is accomplished. The component for providing ozone and operation thereof are the same as those of the first sterilization step. Also, as in the first sterilization step, the third sterilization step is accomplished under the condition where the pressure inside the sterilization chamber 2 is above atmospheric pressure. In this embodiment, the pressure is 1500 torr. Accordingly, sterilization efficiency of the sterilization subject can be maximized as compared to the conventional sterilization by which sterilization is carried out under the condition where the pressure inside the chamber is below atmospheric pressure.

After carrying out the third sterilization step for a predetermined period of time, the hydrogen peroxide and ozone used in the sterilization process is discharged out of the sterilization chamber 2. Prior to the discharge of ozone, the hydrogen peroxide and ozone inside the sterilization chamber 2 need to be decomposed into unharmful substance. To this end, while the hydrogen peroxide and ozone inside the sterilization chamber 2 is discharged, the hydrogen peroxide and ozone are passed through a hydrogen peroxide decomposer 6 and the ozone decomposer 7 in order to them to unharmful substance (second decomposition step). Thus decomposed unharmful gas is completely discharged out of the sterilization chamber 2 by the operation of the vacuumization accelerator 4, and the pressure inside the sterilization chamber 2 is decreased to a substantial vacuum (second vacuumization step). In FIG. 2, the step during which the hydrogen peroxide and ozone inside the sterilization chamber 2 are decomposed and the pressure inside the sterilization chamber 2 is decreased is represented as "$H_2O_2/O_3$ decomposition" step. As described earlier, the discharge of the gas remaining inside the sterilization chamber 2 and the lowering of the pressure inside the sterilization chamber 2 are to maximize sterilization efficiency of the steriliant, i.e., ozone and/or hydrogen peroxide, to be provided subsequently.

In order to ensure sufficient sterilization of the sterilization subject held in the sterilization chamber 2, the aforesaid second sterilization step and the $H_2O_2/O_3$ decomposition step may be repeated as desired. In FIG. 2, the second sterilization step, the third sterilization step and the $H_2O_2/O_3$ decomposition step are repeated 2 times. If necessary, including the first sterilization step and the $O_3$ decomposition step, the process from the first sterilization step through the $H_2O_2/O_3$ decomposition step may be repeated.

Following the $H_2O_2/O_3$ decomposition step after sterilization is completed as desired, a pressure restoration step is carried out in order to restore the pressure inside the sterilization chamber 2 to atmospheric pressure, so that the sterilization subject can be taken out easily from the sterilization chamber 2 by opening the chamber door 21 of the sterilization chamber 2. As described earlier, the pressure restoration step is accomplished by operating the pressure restorer 8.

Figure 3:
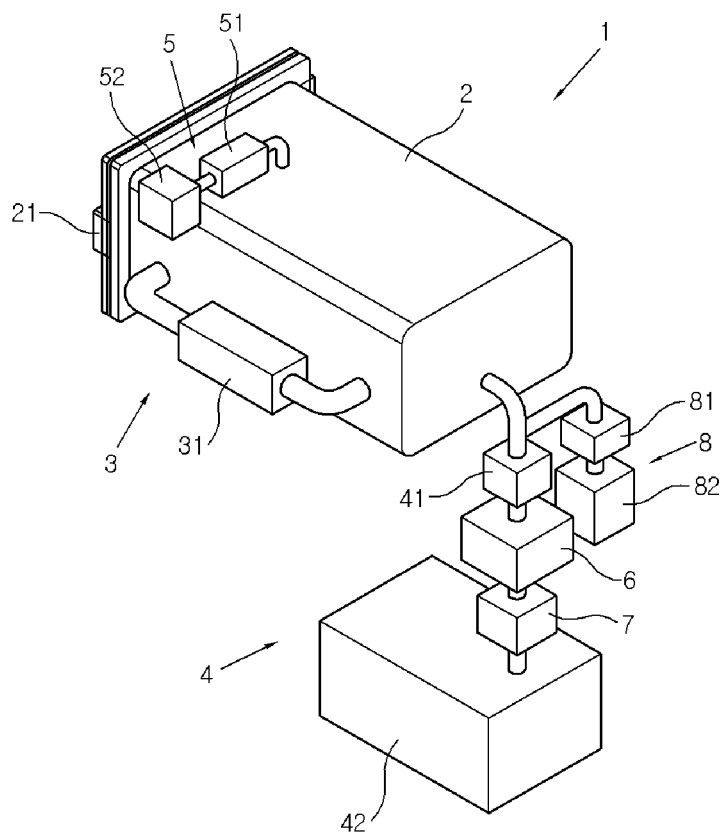
FIG. 3 schematically illustrates a mixed sterilization apparatus according to another embodiment of the present invention.
Figure 4:
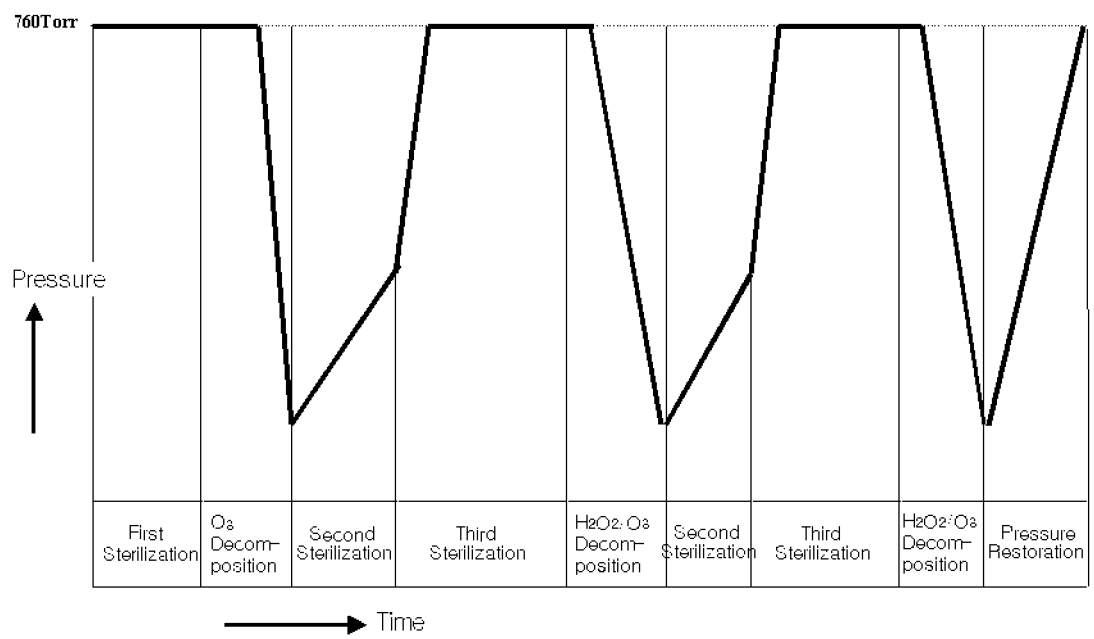
FIG. 4 is a pressure-time graph of a sterilization process using the mixed sterilization apparatus of FIG. 3.

FIG. 3 and FIG. 4 illustrate a mixed sterilization apparatus 1 and a sterilization method according to another embodiment of the present invention.

The construction of the mixed sterilization apparatus 1 illustrated in FIG. 3 is identical with that of the mixed sterilization apparatus 1 illustrated in FIG. 1, except for the ozone compressor 3. Accordingly, the same reference numerals will be used for the elements corresponding to those of FIG. 1, and description thereof will be omitted.

The ozone compressor 3 illustrated in FIG. 3 does not generate ozone to be provided into the sterilization chamber 2 by converting an oxygen-containing substance outside the sterilization chamber 2, but converts oxygen included in the air existing inside the sterilization chamber 2 to ozone and provides it again into the sterilization chamber 2. Accordingly, the ozone compressor 3 illustrated in FIG. 3 does not require the air supply pump 32 or the filter 33, which are used to suck in oxygen from the outside oxygen-containing substance as in FIG. 1. It is simply constructed by connecting the inlet and outlet of the ozone generator 31 to the sterilization chamber 2.

Now, a sterilization process using the mixed sterilization apparatus 1 of FIG. 3 will be described referring to FIG. 4.

Figure 2:
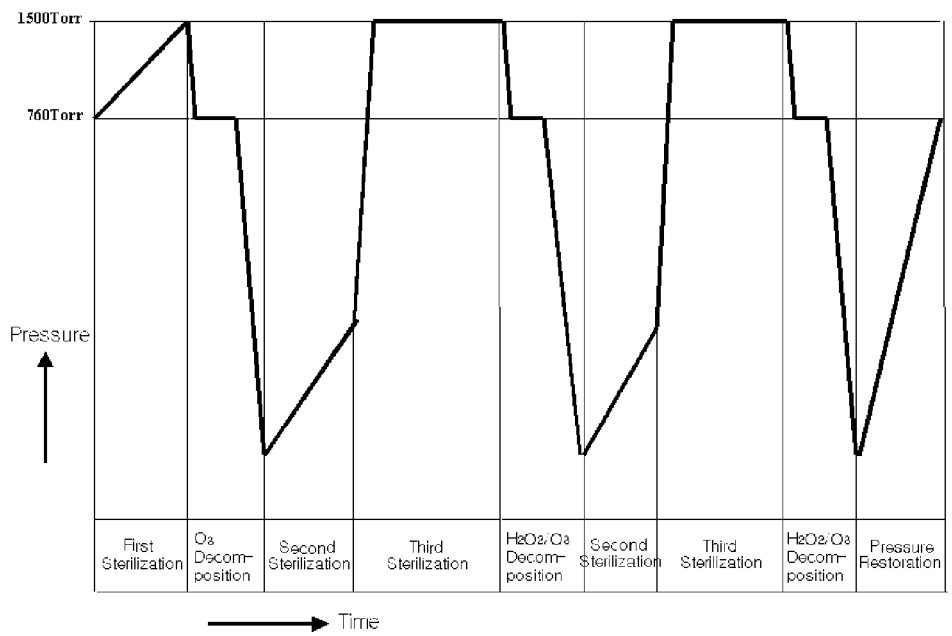
FIG. 2 is a pressure-time graph of a sterilization process using the mixed sterilization apparatus of FIG. 1.

The sterilization process illustrated in FIG. 4 is similar to the sterilization process illustrated in FIG. 2, except that each sterilization step is carried out at atmospheric pressure or at a pressure substantially the same as atmospheric pressure.

A first sterilization step is begun after a sterilization subject is held in a sterilization chamber 2 and the sterilization chamber 2 is sealed off. In a first sterilization step, an ozone compressor 3 converts oxygen included in the air inside the sterilization chamber 2 to ozone and provides it again into the sterilization chamber 2. At this time, the pressure inside the sterilization chamber 2 is maintained substantially the same as atmospheric pressure, but it may decrease below atmospheric pressure when the first sterilization step is continued for a long time.

After the first sterilization step is completed, an ozone decomposition step, a second sterilization step, a third sterilization step, and an $H_2O_2/O_3$ decomposition step are carried out, which are the same as described referring to FIG. 2. However, as described above, in the third sterilization step, the pressure inside the sterilization chamber 2 is substantially the same as atmospheric pressure.

Figure 5:
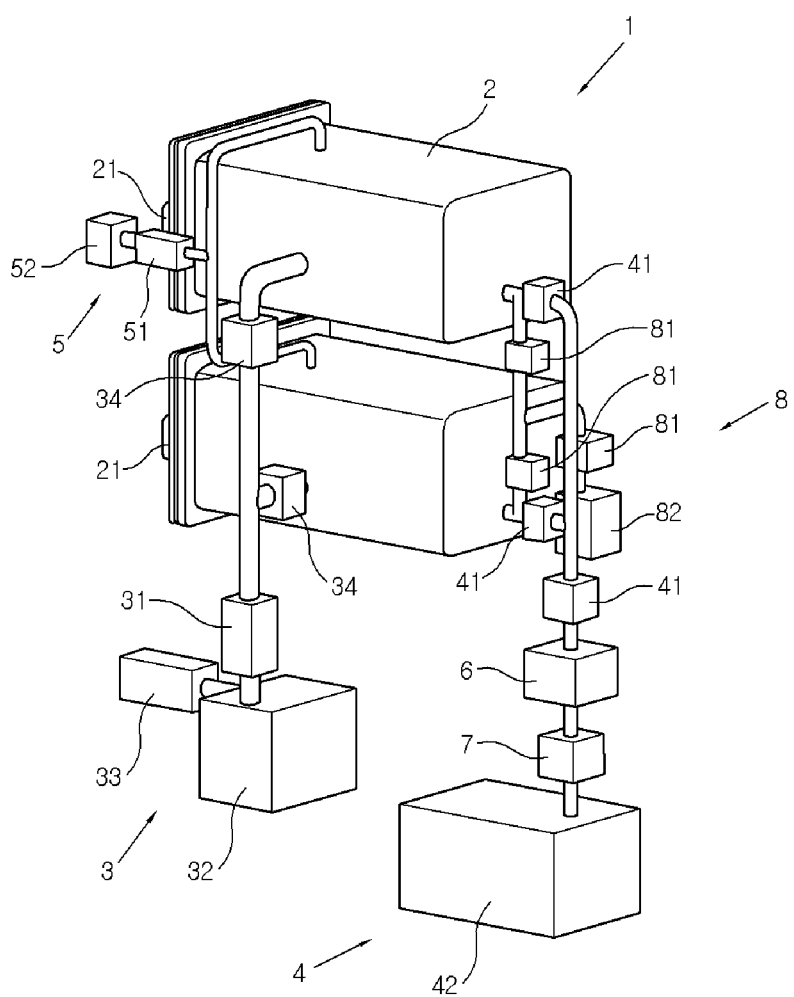
FIG. 5 schematically illustrates a mixed sterilization apparatus of FIG. 1 according to a modified embodiment.
Figure 6:
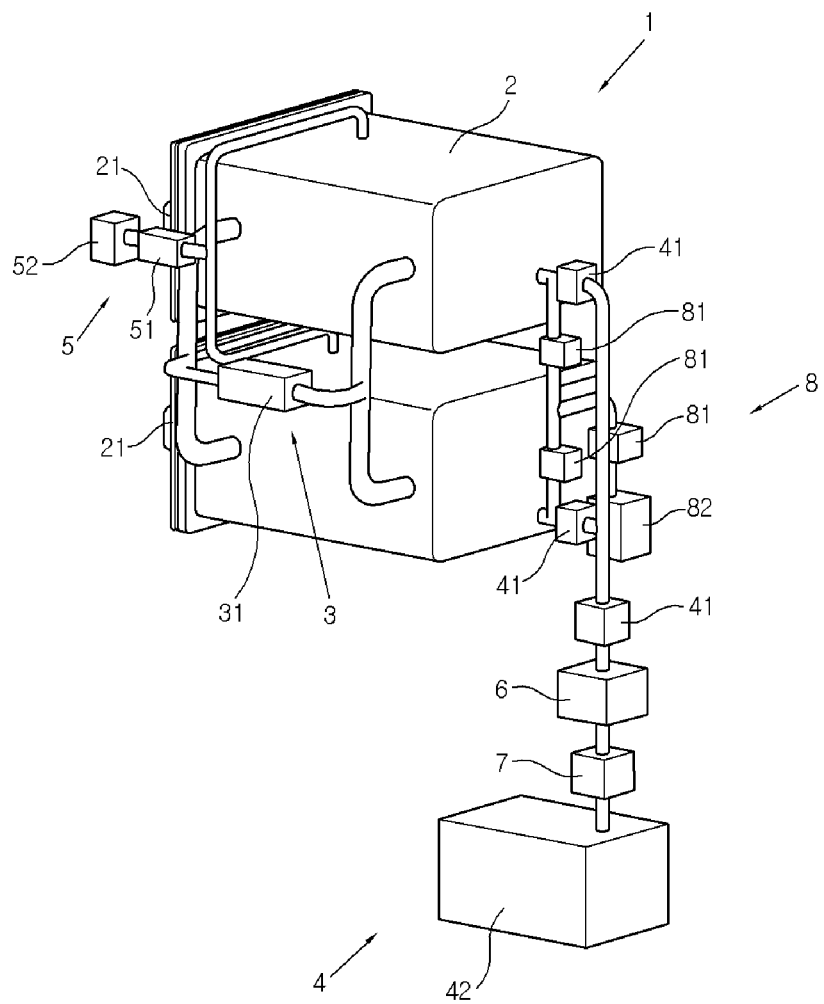
FIG. 6 schematically illustrates a mixed sterilization apparatus of FIG. 3 according to a modified embodiment.

FIG. 5 and FIG. 6 illustrate the embodiments in which the number of the sterilization chamber 2 of the mixed sterilization apparatus 1 illustrated in FIG. 1 and FIG. 3 is increased to two, respectively. Also, more than two sterilization chambers 2 may be used. In FIG. 5 and FIG. 6, an ozone compressor 3, a vacuumization accelerator 4, a hydrogen peroxide compressor 5, a hydrogen peroxide decomposer 6, an ozone decomposer 7 and a pressure restorer 8 are shared by the two sterilization chambers 2. In another embodiment, some of the aforesaid components may be provided with the same number as the sterilization chamber 2, so that they can be used separately by each of the sterilization chambers 2.

In general, a sterilization apparatus requires at least 20 to 30 minutes of sterilization time. When a plurality of sterilization chambers are used, sterilization time can be reduced as compared when only one sterilization chamber is used. For instance, even when a sterilization process is being carried out in one sterilization chamber, another sterilization process may be started in another sterilization chamber. Therefore, the sterilization of other medical instruments can be started without having to wait until the operation of the sterilization chamber is finished. Further, although a plurality of sterilization chambers are used, the components connected to the sterilization chambers, i.e., vacuumization accelerator, steriliant supplier, steriliant decomposer, pressure restorer, etc., can be used commonly, manufacturing cost of the sterilization apparatus can be reduced while significantly reducing sterilization time.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for sterilization using hydrogen peroxide and ozone, in the sequence set forth, comprising:
    a first sterilization step of providing a sterilization subject in a sealed sterilization chamber and sterilizing the sterilization subject by providing ozone inside the sterilization chamber;
    a first decomposition step of decomposing the ozone inside the sterilization chamber;
    a first vacuumization step discharging the gas inside the sterilization chamber and reducing the pressure inside the sterilization chamber;
    a second sterilization step of providing hydrogen peroxide into the vacuumized sterilization chamber to sterilize the sterilization subject;
    a third sterilization step of providing ozone into the sterilization chamber;
    a second decomposition step of decomposing the hydrogen peroxide and the ozone inside the sterilization chamber;
    a second vacuumization step of discharging the gas inside the sterilization chamber and reducing the pressure inside the sterilization chamber; wherein the first sterilization step and the third sterilization step are carried out under the condition where the pressure inside the sterilization chamber is atmospheric pressure or higher, and the ozone provided in the first sterilization step and the third sterilization step is produced by converting an oxygen-containing substance outside the sterilization chamber or oxygen contained inside the sterilization chamber; and wherein
    said method does not involve plasma inside the sterilization chamber.

2. The method for sterilization as set forth in claim 1, wherein the steps from the first sterilization step through the second vacuumization step is repeated until a wanted degree of sterilization is attained.

3. The method for sterilization as set forth in claim 1, further comprising a pressure restoration step of restoring the pressure inside the sterilization chamber to atmospheric pressure after the second vacuumization step.

4. The method for sterilization as set forth in claim 1, wherein
   the first sterilization step and the third sterilization step are carried out under the condition where the pressure inside the sterilization chamber is atmospheric pressure, and the ozone provided in the first sterilization step and the third sterilization step is produced by converting the oxygen contained inside the sterilization chamber.

5. The method for sterilization as set forth in claim 1, wherein the pressure inside the sterilization chamber is about 2 times the atmospheric pressure.

6. A method for sterilization using hydrogen peroxide and ozone, in the sequence set forth, comprising:
   a first sterilization step of providing a sterilization subject in a sealed sterilization chamber and sterilizing the sterilization subject by providing ozone inside the sterilization chamber;
   a first decomposition step of decomposing the ozone inside the sterilization chamber;
   a first vacuumization step discharging the gas inside the sterilization chamber and reducing the pressure inside the sterilization chamber;
   a second sterilization step of providing hydrogen peroxide into the vacuumized sterilization chamber to sterilize the sterilization subject;
   a third sterilization step of providing ozone into the sterilization chamber;
   a second decomposition step of decomposing the hydrogen peroxide and the ozone inside the sterilization chamber;
   a second vacuumization step of discharging the gas inside the sterilization chamber and reducing the pressure inside the sterilization chamber; wherein
   the first sterilization step and the third sterilization are carried out under the condition where the pressure inside the sterilization chamber is higher than atmospheric pressure, and
   the ozone provided in the first sterilization step and the third sterilization step is produced by converting the oxygen-containing substance outside the sterilization chamber.

* * * * *